US006554846B2

(12) United States Patent
Hamilton et al.

(10) Patent No.: US 6,554,846 B2
(45) Date of Patent: Apr. 29, 2003

(54) SONIC BURR

(75) Inventors: Eric B. Hamilton, Washougal, WA (US); Tim Johnson, Seatac, WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 50 days.

(21) Appl. No.: 09/967,444

(22) Filed: Sep. 28, 2001

(65) Prior Publication Data

US 2003/0065350 A1 Apr. 3, 2003

(51) Int. Cl.[7] ................................ A61B 17/22
(52) U.S. Cl. ....................... 606/159; 606/171
(58) Field of Search ................. 606/159, 169, 606/171, 32, 39, 45; 604/22; 600/471, 439

(56) References Cited

U.S. PATENT DOCUMENTS

| | | | |
|---|---|---|---|
| 4,990,134 A | 2/1991 | Auth | |
| 5,100,424 A * | 3/1992 | Jang et al. | 606/159 |
| 5,100,426 A | 3/1992 | Nixon | |
| 5,240,004 A | 8/1993 | Walinsky et al. | |
| 5,314,407 A | 5/1994 | Auth et al. | |
| 5,314,438 A * | 5/1994 | Shturman | 606/159 |
| 5,609,606 A | 3/1997 | O'Boyle | |
| 5,681,336 A | 10/1997 | Clement et al. | |
| 5,725,494 A | 3/1998 | Brisken | |
| 5,846,218 A | 12/1998 | Brisken et al. | |
| 6,004,269 A | 12/1999 | Crowley et al. | |
| 6,083,232 A | 7/2000 | Cox | |
| 6,206,898 B1 | 3/2001 | Honeycutt et al. | |
| 6,235,024 B1 * | 5/2001 | Tu | 604/22 |
| 6,394,956 B1 * | 5/2002 | Chandrasekaran et al. | 600/439 |

\* cited by examiner

Primary Examiner—Julian W. Woo
(74) Attorney, Agent, or Firm—Christensen O'Connor Johnson Kindness PLLC

(57) ABSTRACT

An ablative burr (100) that may be used for a medical procedure, such as an atherectomy, that does not require the user of an elongate flexible drive shaft. The burr comprises a main body (110) that is elastically connected to an abrasive shell member (130). One or more oscillatory driver(s) (150), such as a piezoelectric transducer, is disposed between the shell member and the main body to oscillate the shell with respect to the main body. Elastically compressible members (140, 142) are provided between the shell member and the main body member. The oscillatory drivers are preferably set or tuned to operate at a resonant frequency of the shell member whereby shell member amplitudes larger than the oscillatory driver amplitudes may be induced. Embodiments of longitudinally oscillatory burrs (100, 200) and rotationally oscillatory burrs (300, 400) are disclosed.

17 Claims, 4 Drawing Sheets

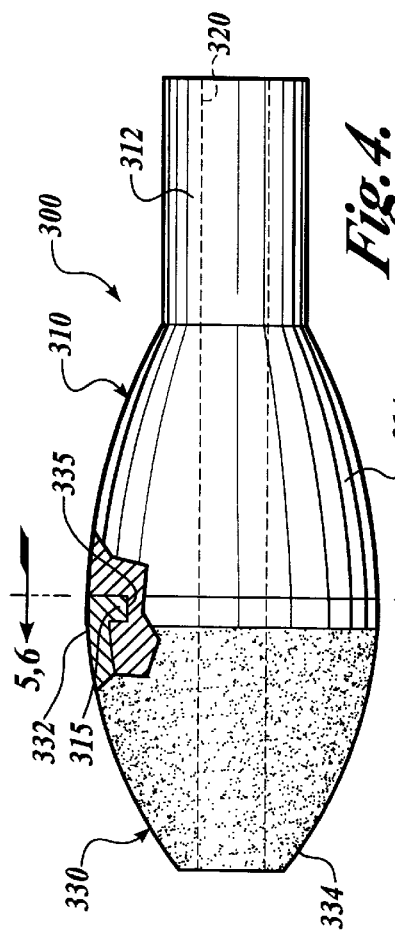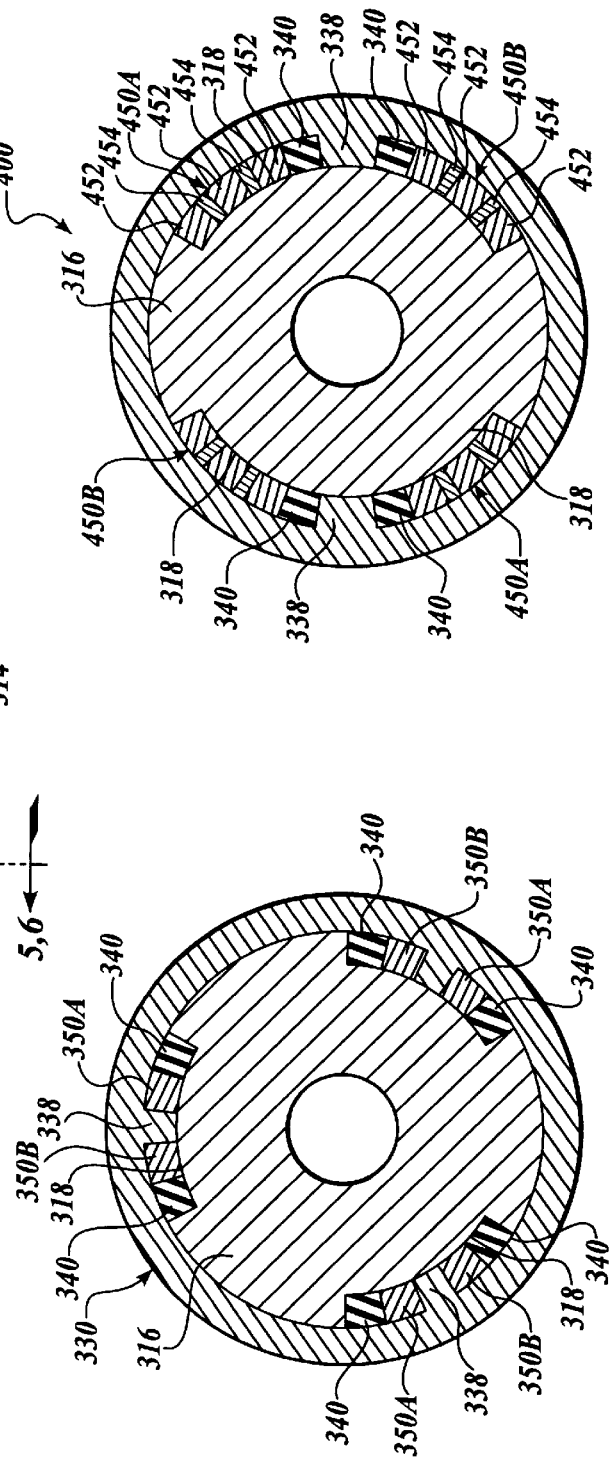

SONIC BURR

FIELD OF THE INVENTION

This invention relates to ablative burrs for medical procedures and, in particular, to an ablative burr for performing an atherectomy procedure.

BACKGROUND OF THE INVENTION

A number of vascular diseases, such as atherosclerosis, medial sclerosis, arteriolosclerosis, and thrombosis are characterized by the buildup of deposits (atheromas), clots, or growths in or on the intimal layer of a patient's blood vessels. Such deposits generally result in occlusions in a person's vascular system that can impede the flow of blood to the affected portion of the person's body. If the occlusion is not removed or otherwise ameliorated, enlargement of the occlusion can result in the complete stoppage of blood flow to the affected region. This can be particularly serious, of course, if the occlusion occurs in a portion of the vasculature that supplies vital organs with blood or other.necessary fluids.

To treat such diseases, many invasive and noninvasive techniques and therapies have been developed. For example, cardiac bypass surgery is now a commonly performed procedure wherein an occluded cardiac artery is bypassed with a segment of a healthy blood vessel that is obtained from elsewhere in the body. While this procedure is frequently successful, it is extremely traumatic to the patient because the entire chest cavity must be opened to access the site of the occluded artery. Because of the trauma and substantial risks associated with cardiac bypass surgery, this procedure may not be a viable option for certain patients, particularly for elderly or relatively frail patients.

As an alternative to cardiac bypass surgery, numerous atherectomy (atheroma removal) devices have been developed for removing such deposits in a less invasive manner. One such device that is particularly suited to removing calcified atherosclerotic plaque is an ablative rotational atherectomy device, such as that disclosed in U.S. Pat. Nos. 4,990,134 and 5,314,407, both to Auth. Auth teaches using a small burr covered, or partially covered, with an abrasive cutting material, such as diamond grit. The burr is attached to the distal end of a flexible, rotatable drive shaft that can be slidably inserted over a guide wire that is inserted through the vasculature of a patient to the site of an occlusion. A rotational atherectomy device practicing the Auth invention is sold by the assignee of the present invention under the trademark Rotablator® and is described below.

Refer now to FIG. 1, depicting the Rotablator ablative rotational atherectomy device 10. This prior art device utilizes a guide wire 26 that is inserted through the patient's vasculature approximately to the location of the deposit that is to be treated. A hollow, flexible drive shaft 22 having an ablative burr 24 at its distal end is then inserted over the guide wire 26, and advanced to a location just proximal to the deposit. The drive shaft 22 is covered with a lumen or catheter 20 along most of its length to minimize the impact to surrounding tissue when the drive shaft 22 is rotatably engaged. The drive shaft 22 is connected to a compressed-air driven drive assembly 16 having a turbine (not shown) that can rotate the drive shaft 22 at relatively high rotational speeds. The drive assembly 16 is slidably mounted in an advancer housing 12 on a track, allowing a surgeon using the Rotablator device 10 to move the drive assembly 16 transversely, and hence move the drive shaft 22 and burr 24 forward and backward to impact and ablate the atheroma.

Rotational ablative atherectomy devices such as the Rotablator® have proven to be effective in treating various types of atheroma. Use of the device, however, requires that a guide wire, drive shaft, and catheter be inserted into the patient and maneuvered through the patient's vasculature to the site of the deposit. It is desirable to minimize the diameter of the catheter in order to facilitate insertion of the device through the patient's vasculature. The minimum diameter of the catheter, however, is limited by the diameter of the drive shaft. The drive shaft, extending from outside the patient up to the atherectomy burr, is then driven externally to provide the driving force to the burr for performing the ablative atherectomy procedure. The patient's vasculature may follow a tortuous path between the point of insertion of the drive shaft and the situs of the atheroma. The drive shaft must be very flexible to negotiate such tortuous path. Moreover, rotation of the in situ drive shaft may generate undesirable stresses on the patient's vasculature.

It would be beneficial to reduce the diameter of the catheter that must be inserted through the patient's vasculature and, in particular, to eliminate the drive shaft that drives the burr.

SUMMARY OF THE INVENTION

The present invention overcomes many of the disadvantages of the prior art by providing an ablation burr that does not require the insertion and operation of a flexible drive shaft through the vasculature of the patient to the sight of the occlusion. The ablation burr according to the present invention utilizes a two-piece burr having a rearward piece attached to a small catheter and an abrasive forward piece elastically connected to the rearward piece. Oscillatory drivers are provided between the forward and rearward pieces that force the forward piece to oscillate. By forcing the forward piece at a resonant frequency, relatively large amplitude oscillatory motion of the forward piece can be achieved.

In an embodiment of the present invention, an ablative burr includes a main body member, a shell member longitudinally coupled to the main body member, and an oscillatory driver disposed between the main body member and the shell member that is adapted to vibrate the shell member at a predetermined frequency. The main body member includes a narrow proximal portion that is attachable to a catheter, an aft-body portion and a coaxial distal portion. The shell member extends around the distal portion and is longitudinally and elastically restrained by the main body member.

In an embodiment of the invention, the oscillatory driver includes an annular piezoelectric transducer that is situated between the main body member and the shell member, and oscillates the shell member longitudinally at a resonant frequency of the shell member.

In another embodiment of the invention, the oscillatory driver includes a plurality of annular piezoelectric transducers that are coaxially stacked with electrode plates therebetween, to produce a cumulative forcing amplitude.

In an aspect of the invention, flexible annular washers are provided between the main body member and the shell member.

In another embodiment of the invention, the oscillatory driver includes at least one elongate piezoelectric transducer situated between the main body member and the shell member, and oscillates the shell member rotationally about its axis at a resonant frequency of the shell member.

In another embodiment of the invention, the oscillatory driver includes a plurality of elongate piezoelectric transducers that are stacked side by side with electrode plates therebetween, to produce a cumulative forcing amplitude.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 4 shows a side view of a circumferentially vibrating ablative atherectomy burr according to the present invention;

FIG. 5 shows a cross sectional front view of the circumferentially vibrating ablative atherectomy burr shown in FIG. 4 through Section 5—5; and FIG. 6 shows a cross-sectional front view of an alternative embodiment of a circumferentially vibrating ablative atherectomy burr shown in FIG. 4 through Section 6—6.

DETAILED DESCRIPTION OF THE PREFERRED EMBODIMENT

Figure 1:
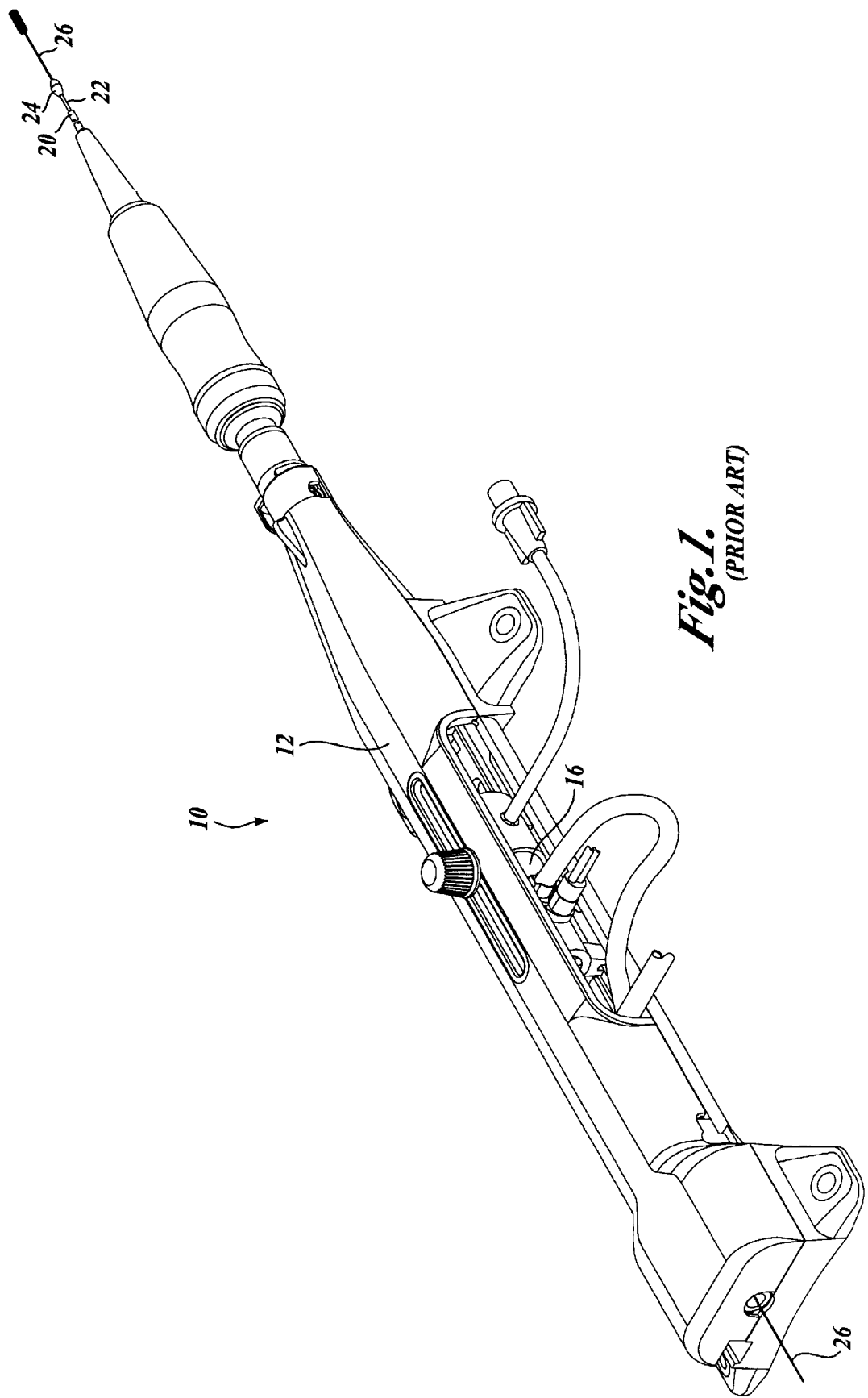
FIG. 1 shows a perspective view of a prior art rotational ablation atherectomy device.
Figure 2:
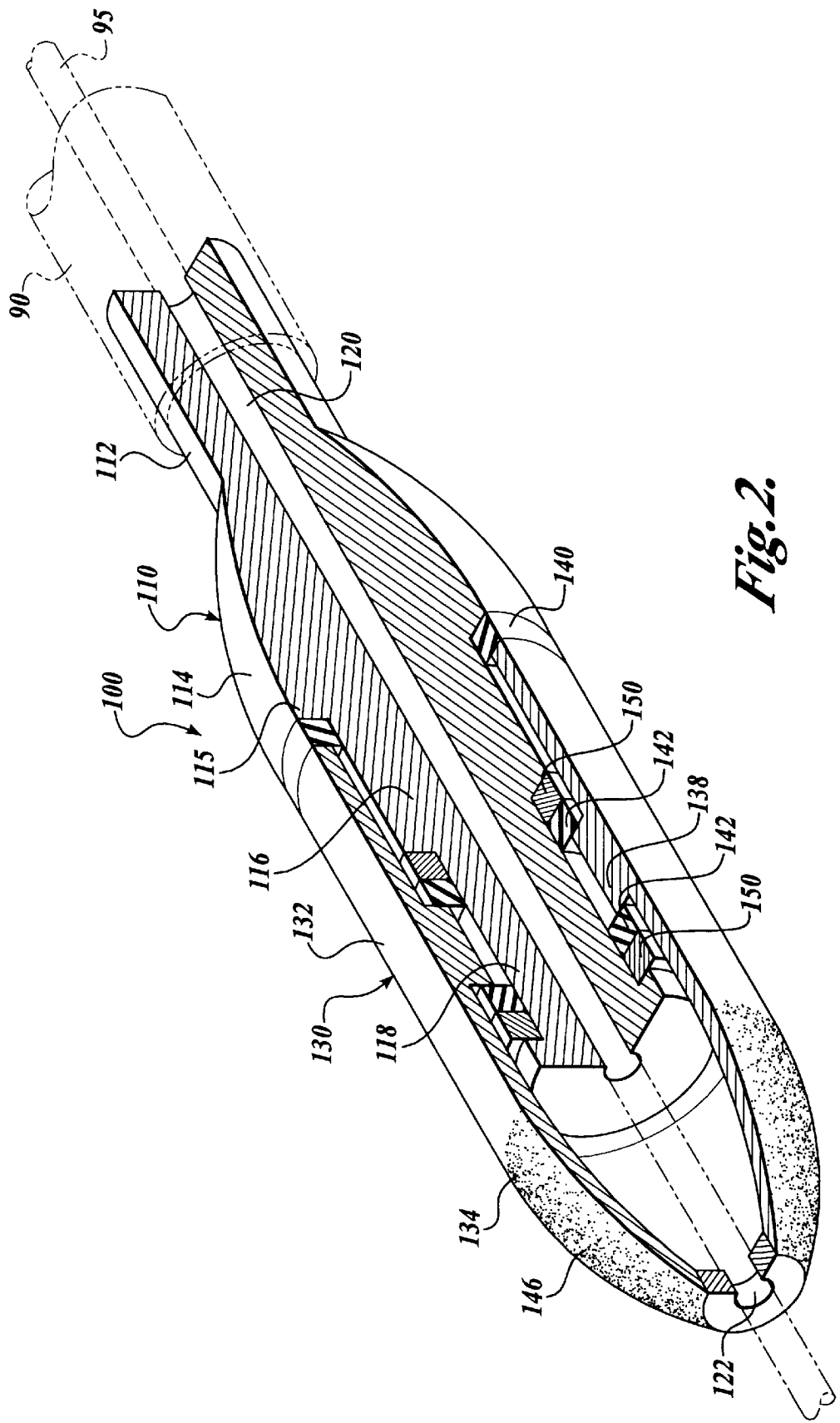
FIG. 2 shows a partially cut-away perspective view of a longitudinally vibrating ablative atherectomy burr according to the present invention.

A first embodiment of an ablative burr according to the present invention is shown in FIG. 2. The burr 100 includes a rearward main body member 110 and a forward shell member 130. The main body member 110 is generally tubular, with a longitudinal central channel 120 that is sized to slidably receive a guide wire 95. The body member has a narrow proximal portion 112, a center aft-body portion 114, and a distal attachment portion 116. The proximal portion 112 is attachable to a small catheter 90 using any conventional attachment method, including for example, bonding, 10 welding, threaded fastening, and the like.

The aft-body portion 114 increases in diameter from the proximal portion 112 up to a maximum diameter at shoulder 115. The attachment portion 116 extends coaxially and forwardly from the aft-body portion 114, and has a smaller diameter than the aft-body portion 114 maximum diameter. The attachment portion 116 has an outwardly-opening circumferential recess 118 extending for a portion of its length.

The forwardly disposed shell member 130 includes a generally tubular proximal portion 132, having a diameter approximately equal to the maximum diameter of the aft-body portion 114 of the main body member 110 and a tapering distal portion 134 extending forwardly from the proximal portion 132. The proximal portion 132 is adapted coaxially engage the attachment portion 116, such that the proximal portion 132 is disposed generally adjacent the aft-body portion 114, as discussed in more detail below. The shell member distal portion 134 includes a center aperture 122 that is axially aligned with the longitudinal channel 120 in the main body member 110, and is sized to slidably receive the guide wire 95. At least some of the distal portion 134 outer surface is provided with an abrasive coating, such as diamond grit 146.

The shell member 130 includes an inwardly disposed circumferential projection 138 having a minimum inner diameter slightly smaller than the maximum outer diameter of the body member attachment portion 116. The shell member 130 is pressed onto the attachment member 116, relying on elastic deformation and/or thermally-induced expansion/contraction of the main body member 110 and the shell member 130, wherein the inwardly disposed projection 138 of the shell member 130 is received and captured by the circumferential recess 118 in the attachment portion 116. Alternatively, the shell member 130 may have one or more longitudinal slots (not shown) and/or the attachment portion 116 may include one or more longitudinal gaps (not shown) to increase the radial flexibility of the respective elements, in order to facilitate assembly of the burr 100.

An elastic annular washer 140 is provided between the proximal end of the shell member 130 and the distal end of the aft-body portion 114, providing an elastically compressible interface therebetween. A pair of smaller elastic annular washers 142 are similarly provided on either side of the shell member's circumferential projection 138, in the circumferential recess 118 of the attachment portion 116. A pair of annular longitudinal oscillatory drivers 150 is installed in the circumferential recess 118 between the outer edges of the recess 118 and the smaller annular washers 142. The shell member circumferential projection 138, smaller washers 142, and oscillatory drivers 150 substantially fill the longitudinal extent of the circumferential recess 118.

The preferred oscillatory driver 150 is a force transducer that converts electromagnetic energy to mechanical ultrasonic vibrations. Suitable force transducers include piezoelectric materials that undergo an elastic strain in response to an applied electric field, such as piezoelectric ceramics and piezopolymers, or magnetostrictors that undergo an elastic strain in response to an external magnetic field. Piezoelectric ceramics include, for example, lead zirconate titinates, and piezopolymers include polyfinyldifluoride. An exemplary magnetostrictive material is $Tb_3Dy_7Fe_2$.

Examining FIG. 2, it will be appreciated that the shell member 130 and the main body member 110 cooperatively form a burr 100 having a generally ellipsoidal outer surface, with a forwardly disposed abrasive portion. The interfaces between the shell member 130 and the main body member 110 include elastic members 140, 142 such that the shell member 130 can oscillate longitudinally with respect to the main body member 110 by the application of appropriate forces produced by the oscillatory drivers 150.

In operation, the burr 100 is disposed near a vascular occlusion, for example, by inserting the guide wire 95 through a portion of the patient's vasculature to the occlusion and then pushing the burr 100 along the guide wire 95 with the catheter 90. The oscillatory drivers 150, which may be attached to an external power source with wires (not shown) slidably disposed in the catheter 90, are then activated with an oscillating current, to longitudinally vibrate the shell member 130 with respect to the main body member 110. The wires may be attached to the oscillatory drivers 150 with any suitable method as is well-known in the art—for example, soldering, brazing, welding, wire bonding, and the like.

The amplitude of the oscillations of piezoelectric oscillatory drivers 150 typically is less than the desired amplitude for ablation burr oscillations. It is known, however, that if a flexible mechanical system is forced or driven at a particular frequency corresponding to a harmonic or resonant frequency for the system, then larger amplitude motions may be induced in the driven mass. This resonant forcing is analogous to pushing a mass on a swing, wherein relatively small amplitude "pushes" can result in large amplitude motion in the mass. The frequency of the driving current is selected to correspond to the resonant frequency for the shell 130. The first and second elastic washers 140, 142 are selected to permit the shell 130 to oscillate with larger amplitudes, when it is driven at its resonant frequency.

It will be appreciated that the burr 100 does not require that a flexible drive shaft be inserted through the patient's vasculature. Rather, relatively small wires are provided to the burr 100 through the catheter 90, to provide electric current to the oscillatory drivers 150. Therefore a smaller catheter may be used, and there is no elongate rotating drive shaft. The burr 100 may therefore be used even if a very tortuous vascular path must be followed to insert the burr 100.

It will be apparent to one of ordinary skill in the art that many variations to the disclosed embodiment could be made without departing from the present invention. For example, the circumferential recess 118 could be disposed on the inside of the shell 130, and the circumferential projection 138 on the attachment member 116, to interlock the burr 100 body and shell. It is also contemplated by the present invention that the abrasive portion of the shell 130 could be produced in many ways, including by machining the shell 130 outer surface, or by affixing abrasive particles other than diamond grit. It is also contemplated that the oscillatory drivers 150 may be attached to a tunable oscillating power source, whereby the optimal forcing frequency can be dialed in during the atherectomy procedure, perhaps utilizing displacement feedback from the burr to optimize the burr's performance.

It is also contemplated that the burr 100 may further include one or more fluid port(s) for aspiration (not shown). The aspiration ports would provide a fluid flow path from the burr 100 to the catheter 90, whereby fluids and entrained particulates may be removed during the atherectomy procedure.

Figure 3:
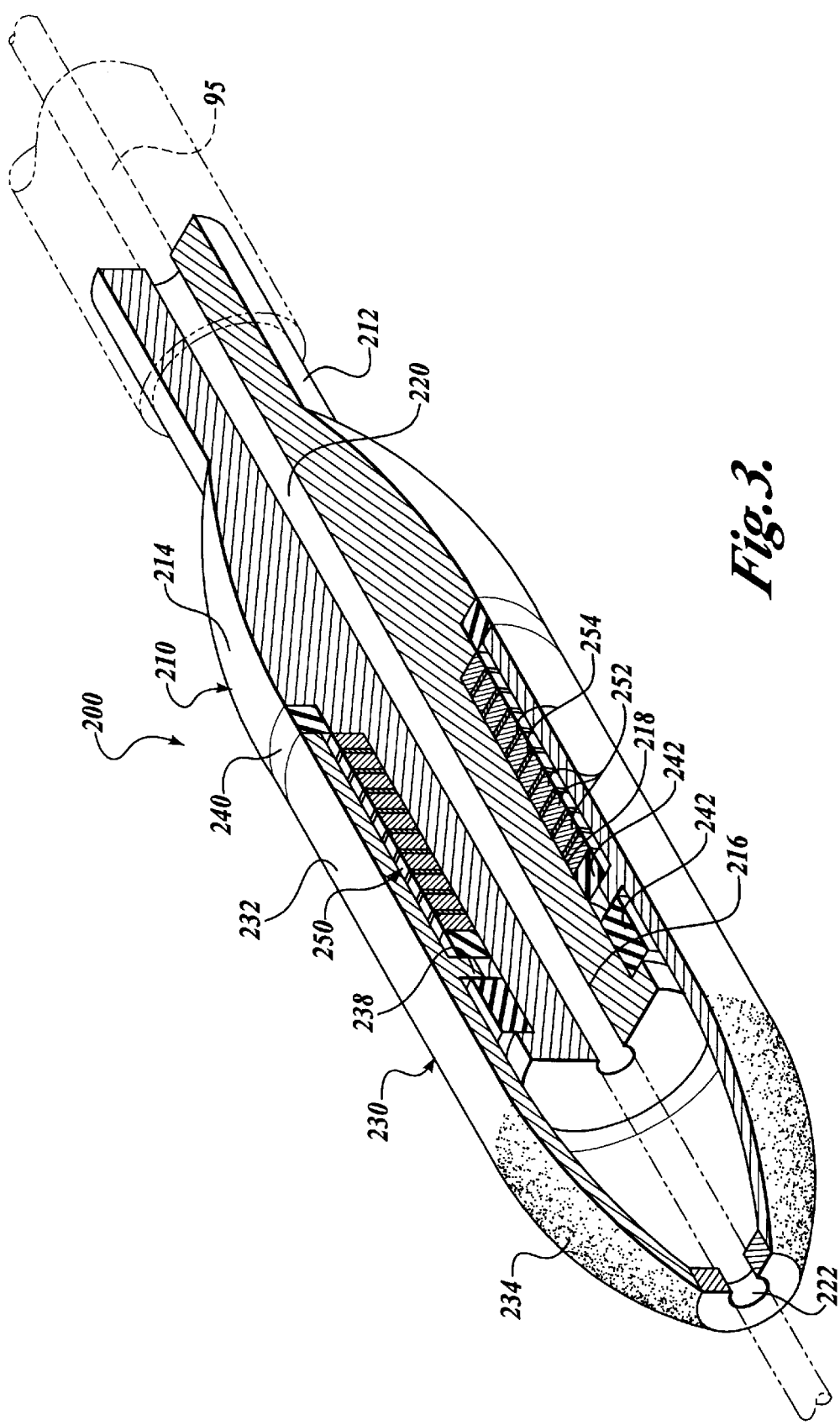
FIG. 3 shows a partially cut-away perspective view of a second embodiment of a longitudinally vibrating ablative atherectomy burr according to the present invention.

FIG. 3 shows a second embodiment of an oscillating burr 200 in accordance with the present invention, utilizing an oscillatory driver 250 made from a stacked arrangement of transducers 252. The burr 200 includes a main body member 210 having a narrow proximal portion 212, a center aft-body portion 214, and a distal attachment portion 216. The distal attachment portion 216 has an outwardly opening circumferential recess 218. A shell member 230 having a proximal portion 232 with an inwardly disposed annular projection 238 and an abrasive tapering distal portion 234 is restrained by the main body member 210, with the annular projection 238 captured within the circumferential recess 218. A longitudinal channel 220 in the main body member 210 is aligned with a center aperture 222 in the shell member 230 to slidably receive the guide wire 95. An elastic annular washer 240 is disposed between the distal end of the aft-body portion 214 and the proximal end of the shell member 230. A pair of smaller elastic annular washers 242 is disposed on opposite ends of the shell member circumferential projection 238.

An oscillatory driver 250 is provided in the circumferential recess 218 of the attachment portion 216, between the shell member 230 and the main body member 210. The oscillatory driver 250 includes a plurality of annular piezoelectric transducers 252 that are stacked in axial alignment, with electrode plates 254 disposed between adjacent transducers 252. The electrode plates 254 are connected to the external power supply (not shown) and are approximately simultaneously subjected to an oscillating current, to simultaneously activate and deactivate the stacked transducers 252, thereby producing a larger amplitude, cumulative longitudinal oscillation. As with the first embodiment discussed above, the oscillatory frequency is preferably selected or tuned to match the resonant frequency of the burr 200 and/or the shell member 230.

A rotationally oscillatory embodiment of an oscillating burr 300 in accordance with the present invention is shown in FIGS. 4 and 5. The burr 300 includes a main body member 310 having a narrow proximal portion 312, a center aft-body portion 314, and a distal attachment portion 316. The distal attachment portion 316 has a plurality of outwardly opening recesses 318 distributed around the circumference of the attachment portion 316. A longitudinal channel 320 is provided through the main body member 310, sized to slidably receive a guide wire (not shown). A circumferential groove 335 is also provided near the distal end of the aft-body portion 314.

A shell member 330 having a proximal portion 332 and a tapering distal portion 334 is rotatably connected to the main body member 310. In the disclosed embodiment, an inwardly projecting lip 315 on the proximal end of the shell member 330 slidably engages a circumferential groove 335 on the main body member 310, thereby rotatably coupling the body and shell members 310, 330. Inwardly disposed longitudinal projections 338 in the shell member 330 engage the recesses 318 in the body member 310. A plurality of elongate elastic members 340 are disposed in the recesses 318 between the main body member 310 and the shell member 330, as seen most clearly in FIG. 5.

A plurality of elongate oscillatory drivers 350A and 350B are provided between the elastic members 340 and the longitudinal projections 338 in the shell, substantially filling the available circumferential extent of the recesses 318. The oscillatory drivers 350 are preferably piezoelectric transducers that are oriented to expand laterally when a current is applied. Applying an oscillating current to the oscillatory driver 350 will cause the shell member 330 to rotate through a small angle with respect to the main body member 310. It will be appreciated, however, that the oscillatory drivers 350A on one side of each longitudinal projection 338 should be energized out of phase with the oscillatory drivers 350B on the opposite side of the longitudinal projections 338. Although the preferred embodiment employs oscillatory drivers 350A, 350B on both sides of each longitudinal projection 338, it will be apparent to one of skill in the art that oscillatory drivers might alternatively be disposed only on one side of the projections 338.

The amplitude of the vibrations in the oscillatory drivers 350 may be smaller than the desired rotational deflections desired in the shell member 330 to achieve the desired ablative effect. As discussed above, however, by driving the shell member 330 at its resonant frequency larger oscillatory motion may be induced in the shell member 330.

The amplitude of the oscillations produced by the vibrating drivers may also be increased by stacking multiple elongate piezoelectric elements side by side, as seen most clearly in FIG. 6. In this fourth embodiment, oscillatory drivers 450A and 450B are made from elongate piezoelectric transducers 452 disposed side by side, with electrode plates 454 between adjacent elements 452. The burr 400 is otherwise substantially identical to burr 300. By simultaneously energizing the piezoelectric transducers 452 on one side of the longitudinal projections 338, the amplitude of the oscillations can be accumulated to increase the effectiveness of the oscillatory drivers 450.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An ablative burr attachable to a flexible catheter and insertable over a guide wire through a portion of a patient's vasculature, the burr comprising:

a main body having a proximal portion adapted to be attached to the flexible catheter and a distal portion extending forwardly from the proximal portion;

a shell member having a rearward portion that extends coaxially around the distal portion of the main body and a tapering forward portion having an abrasive outer surface; wherein the longitudinal position of the shell member with respect to the main body is elastically constrained; and an oscillatory driver disposed between the main body and the shell member adapted to vibrate the shell member with respect to the main body at a predetermined frequency.

2. The ablative burr of claim 1, wherein the oscillatory driver comprises at least one annular piezoelectric transducer.

3. The ablative burr of claim 2, wherein the predetermined frequency of the oscillatory driver is selected to be approximately equal to a resonant frequency of the shell member.

4. The ablative burr of claim 3, wherein the abrasive outer surface of the tubular head comprises a plurality of abrasive particles affixed to the tubular head.

5. The ablative burr of claim 4, wherein the abrasive particles comprise diamond.

6. The ablative burr of claim 3, wherein a plurality of annular elastic washers are disposed between the main body and the shell member.

7. The ablative burr of claim 3, wherein the at least one annular piezoelectric transducer comprises a plurality of stacked annular piezoelectric transducers, and further comprising a plurality of annular electrode plates, each electrode plate being disposed between adjacent piezoelectric transducers.

8. The ablative burr of claim 3, wherein the shell member oscillates longitudinally with respect to the main body.

9. The ablative burr of claim 1, wherein the oscillatory driver comprises at least one elongate piezoelectric transducer.

10. The ablative burr of claim 9, further comprising a plurality of elongate elastic members disposed between the shell member and the main body.

11. The ablative burr of claim 10, wherein the shell member oscillates rotationally with respect to the main body.

12. An ablative atherectomy burr comprising:

a rearward main body member adapted to be attached to a catheter, the main body member having a longitudinal channel therethrough, the main body member including a forwardly extending axial attachment post;

a coaxial shell member having a proximal portion engaging the attachment post and extending forwardly from the body member, the shell member having a tapering abrasive outer surface;

at least one elastically compressible member disposed between the main body member and the shell member such that the shell member can be elastically oscillated with respect to the main body member; and a means for oscillating the shell member with respect to the main body member.

13. The ablative atherectomy burr of claim 12, wherein the means for oscillating the shell member comprises at least one first piezoelectric transducer.

14. The ablative atherectomy burr of claim 13, wherein the first piezoelectric transducer is annular and disposed between the main body member and the shell member such that the shell member is displaced longitudinally when a current is applied to the piezoelectric transducer.

15. The ablative atherectomy burr of claim 14, further comprising a plurality of annular piezoelectric transducers stacked in axial alignment with the first piezoelectric transducer and a plurality of electrode plates, each electrode plate being disposed between adjacent transducers, wherein the plurality of transducers are energized simultaneously to produce a cumulative displacement.

16. The ablative atherectomy burr of claim 13, wherein the first piezoelectric transducer is an elongate transducer that expands laterally when a current is applied.

17. The ablative atherectomy burr of claim 16, wherein the first piezoelectric transducer is disposed between the main body member and the shell member such that the shell member is displaced about its axis when a current is applied to the piezoelectric transducer.

* * * * *